United States Patent [19]

Baker

[11] Patent Number: 4,642,295
[45] Date of Patent: Feb. 10, 1987

[54] METHODS OF DETERMINING FRUCTOSAMINE LEVELS IN BLOOD SAMPLES

[76] Inventor: John R. Baker, 25 Dell Avenue, Remuera, Auckland, New Zealand

[21] Appl. No.: 450,149

[22] Filed: Dec. 15, 1982

[30] Foreign Application Priority Data

Dec. 23, 1981 [NZ] New Zealand .......................... 199380

[51] Int. Cl.$^4$ ....................... G01N 33/66; G01N 33/68
[52] U.S. Cl. ............................................ 436/87; 436/8; 436/14; 436/15; 436/34; 436/88; 436/95; 436/904
[58] Field of Search ................... 436/67, 87, 88, 95, 436/111, 164, 903, 904, 63, 34, 14, 15, 16, 8; 422/61

[56] References Cited

U.S. PATENT DOCUMENTS

| | | | |
|---|---|---|---|
| 3,682,586 | 8/1972 | Ertingshausen et al. | 436/34 |
| 4,200,435 | 4/1980 | Stroupe et al. | 436/67 |
| 4,243,534 | 1/1981 | Bulbenko | 436/67 X |
| 4,268,270 | 5/1981 | Gabbay et al. | 436/67 |
| 4,269,605 | 5/1981 | Dean et al. | 436/67 |
| 4,371,374 | 2/1983 | Cerami et al. | 436/87 |
| 4,399,227 | 8/1983 | Niederau et al. | 436/67 |
| 4,407,961 | 10/1983 | Sanders | 436/67 |
| 4,409,335 | 10/1983 | Hanamoto et al. | 436/67 |

FOREIGN PATENT DOCUMENTS 1135880  5/1957  France .............................. 128/738

OTHER PUBLICATIONS

Bunn et al, Biochemical and Biophysical Research Communications, vol. 67, No. 1, pp. 103-109, 1975.
Mayer et al, Clin. Chim. Acta, vol. 127, pp. 147-184, 1983.
Goldstein, Clinical Diabetes, vol. 4, No. 1, Cover Article, 1986.
Burrin et al, Ann. Clin. Biochem., vol. 22, pp. 327-342, 1985.
Passey et al, Clin. Chem., vol. 23, No. 1, pp. 131-139, 1977.
Mollering et al, "Principles of Enzymatic Analysis", pp. 136-144, section titled, Visualization of NAD(P)-Dependent Reactions.
Kennedy et al, Annals of Internal Medicine, vol. 95, No. 1, pp. 56-58, 1981.
Johnson et al, Clin. Chim. Acta, vol. 127, pp. 87-95, 1982.
Hodge, "Advances in Carbohydrate Chemistry", vol. 10, Published by Academic Press, Inc., New York, 1955, pp. 169-205.
Koenig et al, N. Engl. J. of Medicine, vol. 295, No. 8, pp. 417-420, Aug. 19, 1976.
Parker et al, Clin. Chem., vol. 27, No. 5, pp. 669-672, 1981.
Josef et al, Chemical Abstracts, vol. 82, Abstract No. 82:70120f.
Trivelli et al, N. Engl. J. of Medicine, vol. 284, No. 7, pp. 353-357, Feb. 18, 1971.

*Primary Examiner*—Arnold Turk
*Assistant Examiner*—Robert J. Hill, Jr.
*Attorney, Agent, or Firm*—Holman & Stern

[57] ABSTRACT

The determination of fructosamine levels in at least part of a blood sample for use in detecting diabetes in patients or deciding treatment levels is effected by controlling the temperature and pH of the sample, adding a coloring agent such as a nitro-blue tetrazolium and after a first delay in time taking a first color measurement at a predetermined wavelength and after a second delay in time taking a second color measurement at the predetermined wavelength, then comparing any resultant change between the first and second color measurements with those of standard solutions, the selected timing delays, wavelength, coloring agent and pH conditions being such that any change of color in the coloring agent between the first and second color measurements is caused predominantly by the glucose in the sample that is reacted with an amine group of protein and has undergone a molecular rearrangement to form fructosamine and not materially by any non-specific reducing substance which may be present in the sample.

17 Claims, 3 Drawing Figures

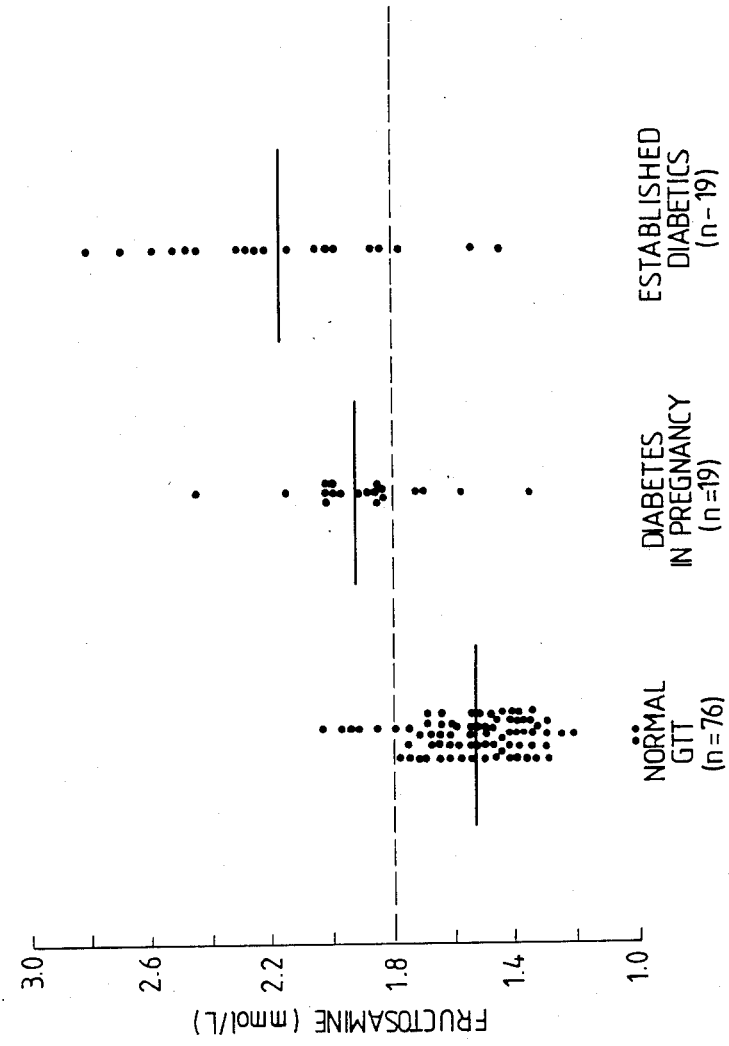

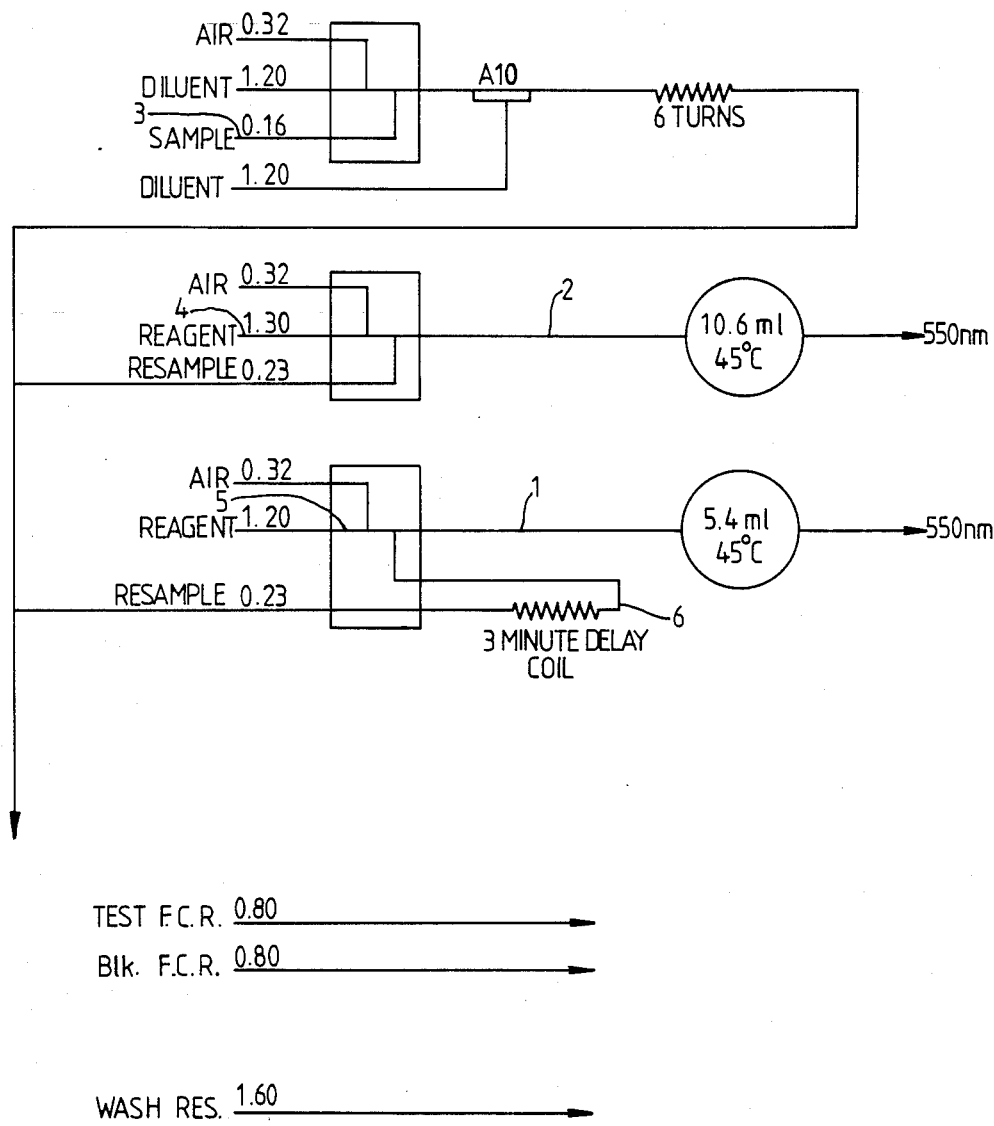
Fig. 3 — SERUM FRUCTOSAMINE ASSAY CONTINUOUS FLOW METHOD

METHODS OF DETERMINING FRUCTOSAMINE LEVELS IN BLOOD SAMPLES

This invention relates to methods of and/or means for determining fructosamine levels in blood samples and has been devised particularly though not solely for use in detecting diabetes in patients and/or deciding treatment levels for diabetes patients.

It is an object of the present invention to provide methods of and/or materials for determining the fructosamine levels in blood samples which will at least provide the public with a useful choice.

Accordingly, one aspect the invention consists of a method of determining serum fructosamine levels in a blood sample or a sample derived from blood, said method comprising the steps of maintaining the sample at a controlled temperature, controlling the pH of the sample to a suitable value, between 10 and 11, adding a colouring agent to the sample and after a first delay in time taking a first colour measurement at a predetermined wavelength and after a second delay in time taking a second colour measurement at the predetermined wavelength and comparing any resultant change between the first and second colour measurements with those of standard solutions, the selected timing delays, wavelength, colouring agent, and pH conditions being such that a change of colour in the colouring agent is caused predominantly by the glucose in the sample that is reacted or associated with an amine group of protein and has undergone a molecular re-arrangement to form fructosamine and not materially by any non-specific reducing substances which may be present in the sample.

In a further aspect, the invention consists of a method of detecting diabetes mellitus in human beings comprising the steps of taking a blood sample or a sample derived from blood from the patient, adding a buffer to adjust the pH of the sample to a suitable value, between 10 and 11, adding a colouring agent to the sample and after a first delay in time taking a first colour measurement at a predetermined wavelength and after a second delay in time taking a second colour measurement at the predetermined wavelength, obtaining corrected readings utilizing the colour measurements and comparing the corrected readings with corrected readings of standards representative of known stages of diabetes mellitus, the selected timing delays, wavelength, colouring agent and pH conditions being such that a change of colour in the colouring agent is caused predominantly by the glucose in the sample that is reacted or associated with an amine group of protein and has undergone a molecular rearrangement to form fructosamine and not materially by any non-specific reducing substances which may be present in the sample.

BRIEF DESCRIPTION OF THE DRAWINGS

Background to the invention and a description of the preferred and alternative embodiments of the invention will now be given with reference to the accompanying drawings in which:

FIG. 2 is a graph of serum fructosamine levels in pregnant patients at 28-32 weeks gestation; and FIG. 3 is a flow diagram of a continuous testing method using the invention.

BACKGROUND TO THE INVENTION

Figure 1:
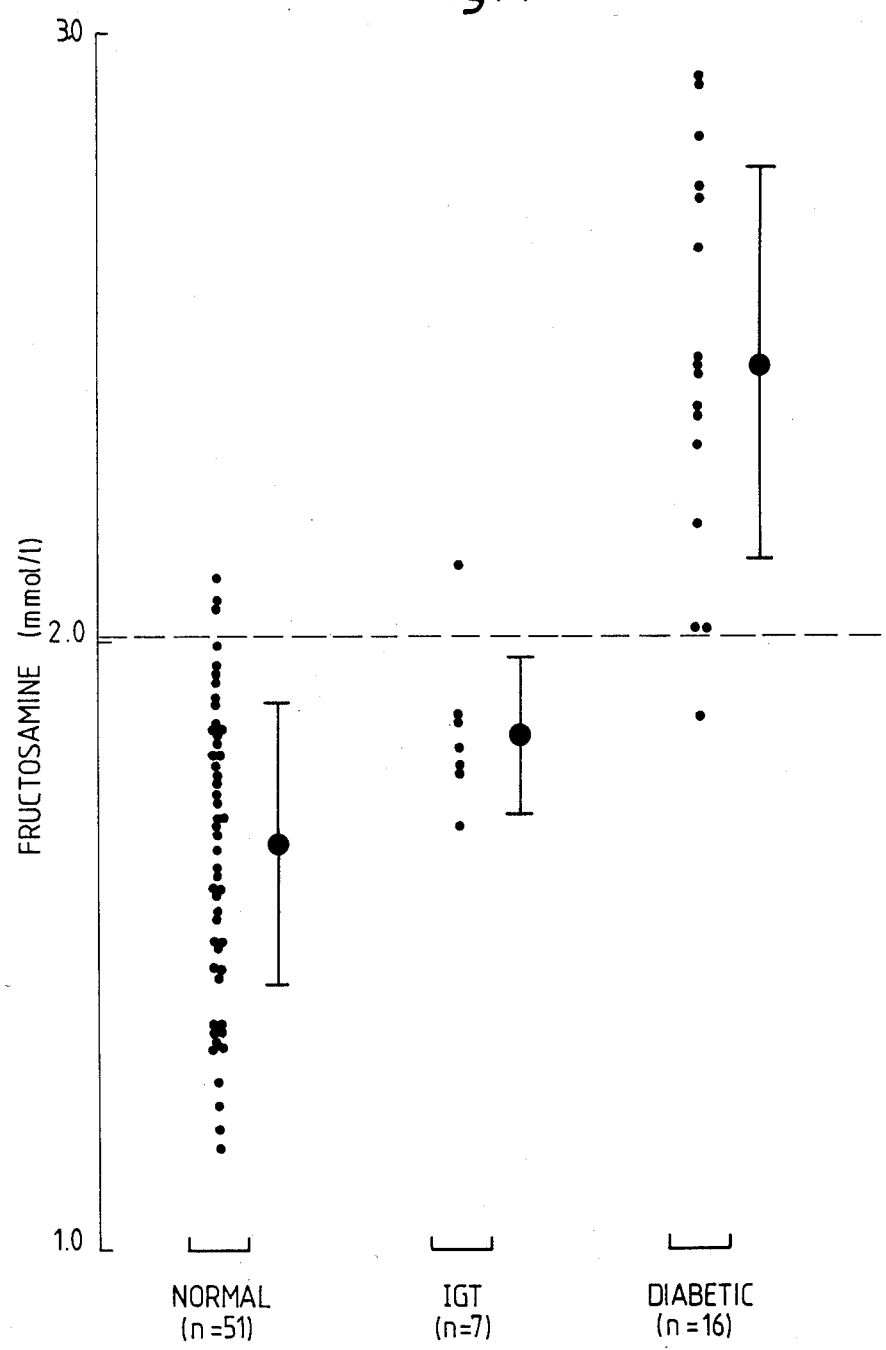
FIG. 1 is a graph of serum fructosamine levels in patients with normal glucose tolerance, impaired glucose tolerance and diabetes mellitus respectively applying WHO criteria for the interpretation of 75 gm glucose tolerance test.

Glycosylation of proteins can occur as a non-enzymic post-translational modification directly dependent upon prevailing glucose concentration. Consequently diabetics tend to have elevated concentrations of glycosylproteins and the degree of glycoslyation of haemoglobin and serum proteins has been correlated with indices of glycaemia.

Because glycosylprotein concentrations reflect an average of serum glucose levels over a period of time, their determination provides an attractive means of monitoring diabetic control and the present invention provides a convenient and practical system for effecting such monitoring.

The present invention makes use of a characteristic of blood that blood glucose reacts continuously with proteins the circulation of in particular human beings in that glucose binds to amino groups of protein to form an aldimine, a Schiff base, which undergoes a molecular (Amadori) rearrangement to form a stable ketoamine (herein generically termed "fructosamine"). The chemistry of this is discussed later in this specification. The present invention at least in the preferred form relates to a colorimetric assay based on the property of fructosamines to act as reducing agents in alkaline solution.

In recent years the major effort in managing diabetes has concentrated on the prevention or amelioration of the chronic complications of diabetes. These complications—retinopathy, nephropathy, neuropathy and artherosclerosis—are derived from prolonged hyperglycaemia, and can be prevented if the blood glucose is maintained as close as possible to normal.

Most of the existing methods for determining the degree of diabetic control are unreliable because they require patient co-operation (e.g. fractional urine collections by the patient at home) or are cumbersome and unreliable (e.g. 24 hour urinary glucose excretion). The blood glucose level fluctuates considerably throughout the day, being influenced by diet, activity, and treatment. Random blood glucose levels have been found to be an inadequate and even misleading index of diabetic control. In the management of established diabetes there is a need for a long term indicator of blood glucose levels. One of the first tests investigated in this context was glycosylated haemaglobin. This test has been useful in the management of diabetes but the test has proved expensive and difficult to reproduce. The need for a more reliable test has led to the present investigation of serum fructosamine. Fructosamine, which is a product of the interaction of serum glucose with serum proteins over days to weeks, meets some of these objections, since it is stable, and does not change with short term fluctuations in blood glucose levels. This test also has the advantage that it is inexpensive, may be automated, and is very reproducible. It can be done on approximately 2 mls of blood.

Fructosamine provides an index of diabetic control that is dependent on the patient's diet, activity or treatment. Its major clinical use is the regulation of treatment for known diabetics and assessment of new treatments. It can also be used to screen populations with an increased risk of developing diabetes—pregnant women, the obese, and the ethnic groups with known tendency to diabetes (e.g. Polynesians). The distinction between the diabetic patient and the patient with normal glucose tolerance test is good, but is less impressive for patients with impaired glucose tolerance.

Over the last year investigations have been done on the levels of serum fructosamine in normal pregnant patients, in pregnant mothers with abnormal glucose tolerance, and those with established diabetes. In normal patients (76 patients with normal glucose tolerance tests evaluated using O'Sullivan's data O'Sullivan J. B., Mahon C. M., Charles D., Dandrow R. (1973) Screening criteria for high risk gestational dibetes patients. Amer. J. Obstet. 116: 895.) the mean serum fructosamine level at 28–32 weeks gestation was 1.51 mmol/l with a standard deviation of 0.24.

Recent fructosamine levels collected at 28–32 weeks gestation in patients with "gestational diabetes" and those with established diabetes have shown that there is a significant difference between the three groups (FIG. 2). The mean fructosamine levels in patients with diabetes diagnosed in pregnancy is 1.91 mmol/l with a standard deviation of 0.23 and in established diabetes is 2.17 with a standard deviation of 0.36. Using a level of 1.8 mmol/l as the upper limit of normal for serum fructosamine, it is possible that its use in a screening test would lead to a detection rate of 80% of diabetes in pregnancy.

DETAILED DESCRIPTION OF THE INVENTION

Glucose bound to serum proteins is measured according to the invention by conversion to its active enol form in alkali, that is to say in a pH which lies between 10 and 14. We have found that different pH levels give different absorbance in the colouring agent used in the method of the invention and accordingly the preferred pH lies between 10.0 and 11.0 and is preferably between 10.5 and 10.8.

The enol form of fructosamine is a chemically active substance and causes a suitable colouring agent to change colour, the colouring agent being preferably a dye selected from tetrazolium salts e.g. tetra nitro blue or preferably nitro-blue tetrazolium which changes to a highly coloured blue (purple) formazan dye having a broad absorbance peak at about 535 nm.

It is part of the invention to avoid interference from other serum reducing substances by measuring the absorbance change at a suitable time after adding the colouring agent. For example, 10 to 15 minutes is allowed to reduce or avoid this interference from other serum reducing substances.

The sample is one derived from blood and preferably is a sample of whole blood or of whole blood serum.

Some precautions are necessary in connection with the blood sample in that moderate to severe haemolysis may give false low results. Although whole blood serum and plasma may be used as the sample material, plasma is much less suitable for the procedure since anticoagulants may interfere with the results.

Samples should preferably be sera with no added preservative.

To provide a suitable pH value in the blood sample, preferably a buffer is added to the blood sample in the form of a solution. The buffer is selected and proportioned to give a pH in the blood sample of between 10.0 and 11.0 preferably between 10.5 and 10.8. This buffer preferably comprises sodium carbonate and sodium bicarbonate in suitable proportions, and we have found that it is preferable to provide the buffer in association with the colouring agent as a single reagent. The buffer desirably contains sodium carbonate in the proportion of 0.795 gm sodium carbonate to 0.210 gm of sodium bicarbonate. Other buffers giving the desired pH may be used. As stated above, the colouring agent is preferably nitro-blue tetrazolium (NBT).

The reagent is mixed with the blood or serum samples and left to stand for a suitable period of time, for example 10 to 15 minutes, before the colour change is measured, for example by measuring the absorbance change using a suitable spectrophotometer.

The measuring of the colour change is preferably checked by using a procedure in which standard solutions are checked for colour readings. The preferred standard solutions comprise a protein such as albumin to which is added a synthetic fructosamine such as 1-deoxy-1-morpholinofructose (DMF). Such standard solutions are preferably prepared by adding aliquots of a 0.01M aqueous solution of 1-deoxy-1-morpholinofructose (DMF) to an albumin solution. The albumin may be albumin 25 g/100 ml (i.e. 250 g/liter, diluted to 40 g/l for use.

These standard solutions are made up in albumin as its presence is necessary to move the peak absorbance of DMF to correspond to that of fructosamine. However, the albumin itself also has some activity and an albumin solution suitably calibrated against the preferred (DMF) standards or calibrated against a protein solution with known $^{14}C$-glucose or $^3H$-glucose incorporated may also be used as standard solutions.

Experiments suggest that the measurements are influenced by reductants of low molecular mass to only a minor degree and are consistent with the notion that NBT reduction reflects mainly the concentration of high molecular mass ketoamines or glycosylproteins, i.e. fructosamine.

When estimated as the change in absorbance at 530 nm over successive five minute intervals between 5 and 20 minutes, NBT reduction is linearly related to DMF concentrations at each time interval, linearity being maintained to 8 mmol of DMF/l, the highest concentration tested. It should be noted that, if plotted, the lines do not pass through the origin as the standard contains 40 g of albumin/l, which itself has some activity.

The methods of the present invention may be performed manually or in automated systems. The assay is simple to do manually and is reproducible. It is also fast. Although in general only 12 samples per hour can be measured where the full time course is recorded in each case, by reading samples every 20 seconds at 10 and 15 minutes in a discontinuous assay, 40 samples per hour can be accommodated.

The reagent comprising the buffer and the colouring agent and the standard solutions comprising a protein such as albumin and a synthetic fructosamine such as 1-deoxy-1-morpholinofructose (DMF) are both novel compositions which form part of the present invention.

Accordingly, the invention also consists of a reagent for use in the methods of the present invention, said reagent comprising a buffer and a colouring agent which changes colour. This reagent, when added to a blood sample or a sample derived from blood, provides colouring agent and pH conditions such that a change of colour in the colouring agent is caused predominantly by the glucose in the sample that is reacted or associated with amine groups of protein and has undergone a molecular re-arrangement to form fructosamine and not materially by any non-specific reducing substances which may be present in the sample.

The invention further consists of a standard solution comprising a protein such as albumin and a synthetic fructosamine such as DMF, preferably a 0.01M aqueous solution of DMF in an albumin solution of 40 g/l concentration.

Changes in the method and materials set forth above may be made while still utilizing the principle of the invention, namely that the enol form of fructosamine is a chemically active substance which converts a suitable colouring agent to give a colour or absorbance change which can be measured and compared with a standard to give an indication of the level of glucose in blood samples even though that glucose remains reacted or associated with protein or amine in the blood and has undergone a molecular re-arrangement to form fructosamine.

To those skilled in the art to which this invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

EXAMPLE 1

Manual Procedure

Materials

Albumin is humam albumin from the Commonwealth Serum Laboratories, Melbourne, Australia and the NBT is from Sigma Chemical Co., St. Louis, Mo., United States of America.

To give a colour reagent: (0.1M $Na_2CO_3$/$NaHCO_3$ pH 10.8), weigh out successively

| | |
|---|---|
| $Na_2CO_3$ | 7.95 g |
| $NaHCO_3$ | 2.1 g |
| Nitro-blue tetrazolium (Sigma) | 0.2 g |
| Ethanol | 40 ml |
| Deionized water | up to 1 liter |

Flush each reagent into a 1000 ml volumetric flask with a little distilled (deionized) water. Dissolve by gently swirling and making up to 1000 ml with distilled water. The pH should be 10.5 to 11.00 and is preferably 10.8. The reagent is not stable at room temperature and should be made up fresh each week or alternatively and preferably is made up in larger quantities, divided into aliguot parts, stored frozen and then thawed before use. The albumin standard comprises albumin 40 g in 1 liter of saline (0.14 m NaCl).

To give 1-deoxy-1-morpholinofructose (DMF) 5 mmol/l standard solutions, 124.5 mgm of DMF (MW249) is weighed out and made up to 100 ml with albumin 40 g/l. The standard is made up in albumin as its presence is necessary to move the peak absorbance of DMF to correspond to that of fructosamine. However, the albumin itself also has some activity and this is subtracted from the standard activity in the calculation shown below.

Standards of concentrations of 1.0; 2.0; 3.0 and 4.00 mmol/l are similarly prepared. The standards are divided into 0.5 ml aliquots and stored at −20° C.

The procedure adopted for measuring fructosamine concentration in blood samples is as follows:

Blood samples are collected in plain tubes, allowed to clot and separated promptly. When not assayed immediately, serum may be kept at <20° C. at which temperature fructosamine is stable indefinitely.

0.1 ml of serum is added to 1 ml of carbonate buffer (0.1 mol/l, pH 10.8) containing 0.25 mmol of nitro-blue tetrazolium (NBT)/l at 37° C., the absorbance at 530 nm is measured at 10 and 15 minutes after mixing and compared with that of standards of 1-deoxy-1-morpholinofructose (DMF) plus albumin (40 g/l) treated in identical fashion. Absorbance is measured in a recording spectrophotometer such as Pye Unicam SP800 or Gilford 250. Reaction rates may, if desired, be followed on a recording spectrophotometer which is thermostatically controlled.

The colour absorbance is first measured at about 530 nm 5–10 minutes after a test has commenced and again 8–15 minutes after said test was commenced and the colour compared with one or more standards of which the relationship between glucose level and colour level is substantially known.

So that timing can be accurately maintained, the serum samples are taken at selected timed intervals, e.g. 15 seconds and 0.1 ml of each serum sample is added to 1.0 ml colour reagent. The absorbance is then read at 530 nm at 5 minutes and 10 minutes or at 10 minutes and 15 minutes from commencement of the test. The albumin and DMF standards are treated similarly to give a check. Corrected readings of fructosamine activity can be calculated as follows (A=absorbance):

$$\frac{(A\ 15\ \text{min} - A\ 10\ \text{mins})\ \text{Test} \times 5}{(A\ 15\ \text{mins} - A\ 10\ \text{mins})\ \text{Std} - (A\ 15\ \text{mins} - A\ 10\ \text{mins})\text{Alb.}} =$$

Fructosamine Conc in Units/l

Ref. Range: 1.40–1.96 Units/l.

NOTES

1. Plasma is less suitable for this test, as anticoagulants may interfere.
2. Specimens are stable at least three months when stored at −20° C.
3. Controls—Commercially available lyophilised sera both bovine and human based provide suitable low, medium and high controls.

EXAMPLE 2

The Determination of Serum or Plasma Fructosamine -Concentration by a continuous flow analyser e.g. a Technicon Auto-Analyser As already noted, albumin bound glucose reduces nitro-blue tetrazolium dye at alkaline pH. Non-specific reduction by other substances goes to completion in a few minutes while fructosamine reduction is ongoing for a much longer time.

As shown in FIG. 3, where a continuous flow apparatus is used, such as a Technicon Auto-Analyser, compensation for non-specific reduction by other substances can be made by using a blank channel 1. The colour change on this channel is read after 5.5 minutes of reaction time while the test channel 2 is read after 8.5 minutes of reaction time. The reaction streams are heated to 45° C. to shorten the peak delay time and the colour reagent contains ethanol in order to linearise the response. The colour is read at 550 nm.

Serum albumin concentration is determined in parallel as the fructosamine level in albumin deficiency states is invalidated.

SYSTEM DESCRIPTION

Referring to FIG. 3 the sample admitted through line 3 is prediluted (1:16) then resampled into the reagent streams 4 and 5. The blank channel incorporates a delay coil 6 with a shorter heating coil so that the reaction time is three minutes less than the test channel, but the total dwell time is the same. The reduction takes place at 45° C., the peaks arrive at the colourimeter simultaneously where the blank reading is automatically subtracted. Exact phasing is achieved with a phasing coil in the blank line, just prior to the colourimeter.

METHOD

1. Select a sampling rate of 75/hr, sample time 40 sec, wash time 8 sec.
2. Connect diluent and NBT reagent to reagent bottles.
3. Turn on pump.
4. Take standards from deep freeze and allow to stand at room temperature.
5. After 10 minutes turn on recorder and set baselines at 10%.
6. Load and run standards, followed by samples. A control is placed every 10 samples.
7. Rinse reagent lines with NaOH (1M) for 5 minutes after last peak has come through, followed by 10 minutes rinsing with water.

BATCH STRUCTURE

| (a) Standard Batch | | |
|---|---|---|
| Cup | Number | |
| 1. | 0 | standard |
| 2. | 1.0 | mmolar std. |
| 3. | 2.0 | mmolar std. |
| 4. | 3.0 | mmolar std. |
| 5. | 4.0 | mmolar std. |
| 6. | 5.0 | mmolar std. |
| (b) Patient Batch | | |
| Cups 5, 25 | LOW CONTROL SERA | |
| Cups 15, 35 | HIGH CONTROL SERA | |
| Cups 10, 20, 30, 40 | REF CONTROL | |

CALCULATION

The standards are made up in albumin solution (40 g/l) and need to be corrected for albumin activity before the standard curve is plotted. The "O" standard is substracted from the other standards and the corrected standards used to prepare the standard curve with the peak heights (y axis) plotted against concentration (x axis).

The sample peaks are read off directly from the standard curve.

REAGENTS

| Diluent | | |
|---|---|---|
| Sodium Chloride (BDH) | 0.9 | g |
| Brij-35 (30%) | 20 | ml |
| Water | to 1 | liter |
| Colour Reagent | | |
| Nitro-blue tetrazolium (Sigma) | 0.20 | g |
| Sodium Carbonate (Riedel-de Haen) | 7.95 | g |
| Sodium Bicarbonate (Riedel-de Haen) | 2.10 | g |
| Water | to 1 | liter |

STANDARDS

A stock solution of 1-deoxy-1-morpholinofructose (DMF) is prepared by weighing 1.245 g of DMF and dissolving in 1 liter of albumin solution. The concentration is 5 mmol/liter.

The albumin solution is prepared by dissolving albumin, 40 g of 1 liter of saline (0.14 m NaCl).

Working standards are prepared from this at concentrations of 1.0; 2.0; 3.0; 4.0 and 5.0 mmol/liter. A blank is prepared using only the albumin diluent with no added DMF.

POINTS OF TECHNIQUE

1. The sampling rate depends on the time taken for the peaks to come to steady state. Some plateau time is required on both test and blank so that they can be phased. Sampling time as little as 30 seconds is sometimes enough, but 40 seconds is better for routine running.
2. Standards contain albumin and need to be refrigerated.
3. The system requires 5 minutes rinse with sodium hydroxide (1M) after each run.

EXAMPLE 3

The Determination of Serum Fructosamine by Bichromatic Discrete Analyser[ABBOTT]

A. Materials (1) Buffer and colour reagent: (0.1M $Na_2CO_3$/$NaHCO_3$ pH 10.57) Weight out successively

| | |
|---|---|
| $Na_2CO_3$ | 0.795 g |
| $NaHCO_3$ | 0.210 g |
| Nitro-blue tetrazolium (NBT) | 0.02 g |

(2) Standard solutions are prepared by adding aliquots of a 0.01M aqueous solution of 1-deoxy-1-morpholinofructose (DMF) to an albumin solution

| | DMF (0.01 M) | Albumin (250 g/l) | 0.14 M NaCl |
|---|---|---|---|
| 0 | 0 | 18 ml | 82 ml |
| 1.0 mmol/l | 10 ml | 18 ml | 72 ml |
| 2.0 mmol/l | 20 ml | 18 ml | 62 ml |
| 3.0 mmol/l | 30 ml | 18 ml | 52 ml |
| 4.0 mmol/l | 40 ml | 18 ml | 42 ml |

The standards are divided into 0.5 ml aliquots and stored at −20° C.

Flush each reagent into a 100 ml volumetric flask with a little distilled water. Dissolve by gentle swirling and make up to 100 ml with distilled water. The pH should be 10.55 to 10.60 and is preferably 10.57. The reagent is not stable indefinitely and should be made up fresh each week or stored at −20° C.

B. Procedure

Conducting a series of tests on an Abbott 200 Bichromatic Analyser is effected as follows:

1. Set up the instruments as follows:

| | |
|---|---|
| Test code | 78 |
| Sample volume | 25 μl (07) |
| Reagent volume | 250 μl (06) |
| Filter | 550/650 |
| Rx Type | Rate |

| | | |
|---|---|---|
| RX Direction | up | |
| Analysis time | 5 minutes | |
| Revolutions | 4 | |
| Temperature | 37° C. | |

2. Use a new clean cuvette.

3. Activate the WASH cycle to flush water through the system and remove bubbles. Working reagent is then substituted for water and PRIME cycle commenced. Discard the first 3 jets, then recycle back into the bottle at least ten times.

4. Insert the required number of sample cups in the carousel and add 50 μl of sample to each cup.

| | |
|---|---|
| 01 | H₂O |
| 02 | zero standard |
| 03 | 1.0 mmol/l |
| 04 | 2.0 mmol/l |
| 05 | 3.0 mmol/l |
| 06 | 4.0 mmol/l |
| 07 | CONTROL SERA |
| 08 | CONTROL SERA |
| 31 | CONTROL SERA |
| 32 | NORMAL control |

09 to 30 are patient specimens. Use a 50 μl positive displacement syringe.

5. A calibration curve is included with each run. Rotate the carousel to position 00 and press the RUN button.

6. The ABA 200 will make 4 revolutions, the first dispensing sample and reagent, the second a delay cycle, the third and fourth initial and final absorbance readings respectively. The difference between the initial and final absorbance readings is used to compute the sample concentration using the standard curve provided.

7. Remove the multicurvette and rinse with water. Leave to soak overnight in water. Flush the pipette with "Contrad" cleaning solution by activating the WASH cycle, and repeat the wash procedure with water.

8. The normal range is 1.14 to 1.96 mmol/l. Diabetic specimens will usually be greater than 2.0 mmol/l.

9. The temperature is controlled, preferably to 37° C.

POINTS OF TECHNIQUE

1. The ABA 200 will automatically reject incorrect RX type Rx direction, temperature, revolution, and time, but NOT incorrect filters or sample/reagent volumes settings.

2. Colour reagent with sodium carbonate/bicarbonate buffer is stable if stored at 4° C. for up to 1 week. Check the pH immediately prior to use and ensure that it is 10.55 to 10.60. Ensure that all NBT is dissolved before using the colour reagent.

3. Control specimens should give values within the 2×SD range in accordance with preferred quality control charts. It is preferable to document all assays where excursion outside the 2×SD range occurs.

4. Samples should be sera with no added preservative.

The methods of the present invention utilise the following chemistry:

Proteins can be glycosylated in vivo by a nonenzymatic reaction between glucose and available amino groups.

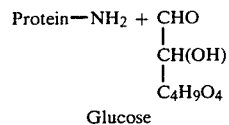

Glucose

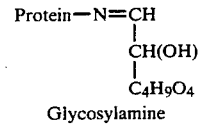

Glycosylamine

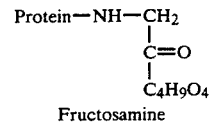

Fructosamine

Glycosylation is dependent upon glucose concentration so that diabetics have higher fructosamine concentrations than normal. Fructosamines in alkaline solution form eneaminols which are reducing substances.

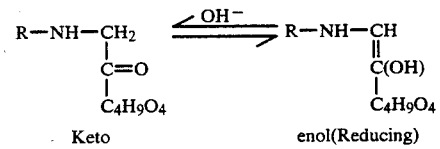

Keto           enol(Reducing)

In the preferred form of the invention, the reducing activity of albumin bound glucose can be detected with nitro-blue tetrazolium at alkaline pH and is measured as a rate of change of absorbance.

From the foregoing it will be seen that the invention at least in the preferred form provides advantages compared with or overcomes disadvantages of present methods.

In particular, the clinical significances of the present invention can be summarised as follow:

1. Fructosamine is an index of metabolic control in patients with diabetes mellitus. It reflects patient compliance, quality of care, and the efficacy of insulin therapy. By use of the present invention fructosamine can be measured at weekly intervals, and it is believed that such measurement accurately and reliably detects improvement/deterioration in diabetic control consequent to a change in management.

2. Fructosamine reflects the glycosylation of serum proteins. The main contribution, greater than 80% is from albumin. The kinetics of its decay approximate the behaviour of albumin. (T1/2=20 days).

3. The value of the test is severely impaired in individuals with hypoalbuminaemia (albumin less than 30 g/l).

4. Fructosamine correlates directly to the fasting blood glucose levels and is relatively less affected by post prandial hyperglycaemia. Sample time and its relation to diet is unimportant.

5. Fructosamine may be useful as a screening test to detect individuals with diabetes mellitus.

6. By conducting the reaction in mild alkaline conditions (pH less than 11.0) and at controlled temperatures (T less than 50° C.) the method according to the invention does not measure free glucose, or glucose in the labile aldimine form but measures only glucose in the stable fructosamine form.

7. By deferring the measurement of colour change for a few minutes after commencing the test, the contribution of interfering substances is minimized.

What is claimed is:

1. A method of determining the level of fructosamine in a blood sample or sample derived from blood wherein the level of fructosamine reflects an average serum glucose level in the sample over a period of time, said method comprising the steps of maintaining the sample at a controlled temperature below 5° C., controlling the pH of the sample to a value between 10 and 11, adding a colouring agent to the sample and after a first delay in time taking a first colour measurement at a predetermined wavelength and after a second delay in time taking a second colour measurement at the predetermined wavelength and determining the fructosamine level in said sample by comparing any resultant change between said first and second colour measurements with those of standard solutions wherein the colouring agent, timing of the delays wavelength and pH conditions selected such that any change of colour in the colouring agent between said first and second colour measurements is caused predominantly by glucose in the sample that is reacted or associated with an amine group of protein and has undergone a molecular re-arrangement to form fructosamine and not materially by any non-specific reducing substances which may be present in the sample.

2. The method as claimed in claim 1 which includes the step of calibrating a testing instrument used during testing of said sample using at least one testing standard which gives a known reading.

3. The method as claimed in claim 1 wherein said pH is controlled by adding to the sample a buffer which includes said colouring agent.

4. The method as claimed in claim 3 in which said buffer comprises sodium carbonate and sodium bicarbonate.

5. The method as claimed in claim 1 wherein said colouring agent comprises a tetrazolium salt which changes colour on being reduced.

6. The method as claimed in claim 5 wherein said colouring agent is nitro-blue tetrazolium.

7. The method as claimed in claim 1 wherein the method steps are carried out in an automatic testing apparatus on a series of samples.

8. The method as claimed in claim 7 wherein said series of samples are maintained at a temperature of about 45° C.

9. The method as claimed in claim 1 wherein said standard solutions comprise aqueous solutions of a protein and 1-deoxy-1-morpholinofructose.

10. The method as claimed in claim 9 wherein said protein is albumin.

11. The method as claimed in claim 1 wherein said first and second colour measurements are obtained by measuring colour absorbances at 530 nm 5–10 minutes and 8–15 minutes respectively after adding the colouring agent to the sample.

12. The method as claimed in claim 11 wherein the method steps are carried out at about 37° C.

13. The method as claimed in claim 11 wherein said colour absorbances are measured about 10 minutes and 15 minutes respectively after adding the colouring agent to the sample.

14. A method of detecting diabetes mellitus by determining the level of fructosamine in a blood sample, comprising the steps of taking a blood sample, maintaining the sample at a controlled temperature below 50° C., controlling the pH of the sample to a value between 10 and 11, adding a colouring agent to the sample and after a first delay in time taking a first colour measurement at a predetermined wavelength and after a second delay in time taking a second colour measurement at the predetermined wavelength, obtaining corrected readings utilizing said colour measurements and comparing the corrected readings with corrected readings of standards representative of known stages of diabetes mellitus, wherein the colouring agent, timing of the delays, wavelength and pH conditions are selected such that any change of colour in the colouring agent between said first and second colour measurements is caused predominantly by glucose in the sample that is reacted or associated with an amine group of protein and has undergone a molecular re-arrangement to form fructosamine and not materially by any non-specific reducing substances which may be present in the sample.

15. The method as claimed in claim 14 wherein said first and second colour measurements are taken at about 5 and 10 minutes respectively after adding said colouring agent to the sample.

16. The method as claimed in claim 14 wherein said colouring agent is a tetrazolium salt.

17. The method as claimed in claim 16 wherein said colouring agent is nitro-blue tetrazolium.

* * * * *